United States Patent [19]

Uno et al.

[11] 4,245,086
[45] Jan. 13, 1981

[54] PRODUCTION OF N-HYDROXYALKYLTRIMELLITIC ACID IMIDES POLYMERS

[75] Inventors: Keiichi Uno; Takahito Miyagawa, both of Otsu, Japan

[73] Assignee: Toyo Boseki Kabushiki Kaisha, Osaka, Japan

[21] Appl. No.: 955,615

[22] Filed: Oct. 30, 1978

Related U.S. Application Data

[63] Continuation of Ser. No. 754,357, Dec. 27, 1976, abandoned.

[30] Foreign Application Priority Data

Dec. 27, 1975 [JP] Japan ................................. 50-158163

[51] Int. Cl.$^3$ .............................................. C08G 73/16
[52] U.S. Cl. ..................................... 528/318; 528/170; 528/274; 528/275; 528/279; 528/281; 528/284; 528/285; 528/289; 528/312; 528/315; 528/319; 528/322
[58] Field of Search ............... 528/170, 289, 322, 274, 528/275, 279, 281, 284, 285, 312, 315, 318, 319

[56] References Cited

U.S. PATENT DOCUMENTS

| | | | |
|---|---|---|---|
| 3,060,191 | 10/1962 | Kolb et al. | 260/326 |
| 3,458,480 | 7/1969 | Schmidt et al. | 528/289 |
| 3,562,219 | 2/1971 | Schmidt et al. | 528/289 |
| 3,567,685 | 3/1971 | Bialous et al. | 528/170 |
| 3,697,471 | 10/1972 | Schmidt et al. | 528/289 |
| 3,880,812 | 4/1975 | Golinkin et al. | 528/289 |
| 3,944,706 | 3/1976 | Czajka | 428/383 |

*Primary Examiner*—Lester L. Lee
*Attorney, Agent, or Firm*—Birch, Stewart, Kolasch & Birch

[57] ABSTRACT

N-Hydroxyalkyltrimellitic acid imides of high purity are prepared by reacting trimellitic acid anhydride with a monoalkanolamine in an aqueous medium comprising an amount of not less than about 0.025 liter of a certain specific solvent or solvent mixture per 1 mole of the trimellitic acid anhydride and can be advantageously used for production of their polymers having a high thermal stability and a good color tone.

9 Claims, No Drawings

PRODUCTION OF N-HYDROXYALKYLTRIMELLITIC ACID IMIDES POLYMERS

This application is a continuation of copending application Ser. No. 754,357, filed on Dec. 27, 1976, and now abandoned.

The present invention relates to production of N-hydroxyalkyltrimellitic acid imides and their polymers. More particularly, it relates to a process for preparing N-hydroxyalkyltrimellitic acid imides (hereinafter referred to as "HATI") of high purity without passing through any specific purification step such as recrystallization and to a process for preparing poly(alkylene-trimetllitate imides) having a high thermal stability (i.e. degradation at melting being reduced) and a good color tone (i.e. abnormal coloring being reduced) from HATI.

In a conventional process for preparation of HATI, of which the most typical example is N-($\beta$-hydroxyethyl)-trimellitic acid imide (hereinafter referred to as "HETI"), the reaction is effected in the presence of dimethylformamide as the reaction medium, and the product is collected from the reaction mixture by elimination of the solvent under distillation and purified by treatment with active carbon and recrystallizing from 1,4-dioxane [Japanese Patent Publication No. 21500/1963]. However, this process requires complicated steps and affords the product only in a poor yield. Moreover, the polymer obtained by polycondensation of such product at a high temperature according to a conventional procedure is extremely colored.

As the result of an extensive study on the production of highly pure HATI, it has been found that the formation of impurities as by-products in the preparation of HATI is attributed largely to self-condensation and amide-binding. On the basis of this finding, attempt has been made to prevent the occurrence of those unfavorable side reactions and the contamination of HATI with unreacted intermediates and by-products. The successful realization of such attempt has lead to completion of the present invention.

According to the present invention, there is provided a process for preparing HATI of high purity which comprises carrying out the reaction of trimellitic acid anhydride with a monoalkanolamine in an aqueous medium comprising an amount of not less than about 0.025 liter of a certain specific solvent or solvent mixture per 1 mole of the trimellitic acid anhydride so as to pass through the stage where the reaction mixture forms a uniform solution, precipitating the produced HATI alone in the reaction mixture and collecting the precipitated HATI.

One of the starting materials in the process of this invention is trimellitic acid anhydride, and the other is a monoalkanolamine. As the monoalkanolamine, there is usually employed a compound having 2 to 10 carbon atoms such as monoethanolamine, mono-n-propanolamine, mono-isopropanolamine, mono-n-butanolamine, mono-n-hexanolamine and 1-hydroxy-2,2-dimethyl-3-aminopropane. The proportion of the trimellitic acid anhydride and the monoalkanolamine is usually from about 10:9 to 8:10, preferably from about 10:10 to 10:11.

The solvents to be used in the process of this invention can be classified into two groups, i.e. (A) solvents which can be in a liquid state at room temperature (25° C.) and have at least one atomic linkage of the formula: X—O—X (wherein X is a hydrogen atom or a carbon atom) (except monohydric alcohols having a boiling point of not higher than 80° C. and ethers having a boiling point of not higher than 60° C.) and (B) solvents which are freely miscible with water at room temperature (25° C.).

Specific examples of the solvents of Group (A) are as follows: (i) water, (ii) monohydric alcohols having not less than 3 carbon atoms such as monohydric aliphatic alcohols of not less than 3 carbon atoms (e.g. n-propyl alcohol, isopropyl alcohol, n-butyl alcohol, isobutyl alcohol, sec.-butyl alcohol, isoamyl alcohol, n-hexyl alcohol, n-octyl alcohol, n-nonyl alcohol, cyclohexyl alcohol, benzyl alcohol), monoesters and monoethers of glycols (e.g. ethylene glycol monomethyl ether, ethylene glycol monoethyl ether, ethylene glycol monobutyl ether, ethylene glycol monophenyl ether, ethylene glycol monoacetate, diethylene glycol monomethyl ether, diethylene glycol monoethyl ether) and monophenolic compounds (e.g. m-methylphenol, o-ethylphenol, m-ethylphenol, p-n-propylphenol, o-isopropylphenol); (iii) dihydric or trihydric alcohols (e.g. ethylene glycol, propylene glycol, 1,4-butylene glycol, diethylene glycol, triethylene glycol, glycerol); (iv) ether compounds (e.g. tetrahydrofuran, dioxane, dipropyl ether, ethyl butyl ether, dibutyl ether, diamyl ether, benzyl ethyl ether, methyl phenyl ether, ethyl phenyl ether), etc. Among them, particularly preferred are water, ethylene glycol, benzyl alcohol and dioxane. Specific examples of the solvents of Group (B) include methanol, ethanol, ethylene glycol, ethylene glycol monomethyl ether (methylcellosolve), ethylene glycol monoethyl ether (ethylcellosolve), dimethylformamide, acetone, dioxane, tetrahydrofuran, etc. These solvents may be used alone or in combination.

By the use of the said solvent (s), the reaction at the initial stage can proceed perfectly since the intermediary amidic acid produced in such stage is easily soluble therein. On the other hand, the produced HATI is hardly soluble in such solvent(s) at room temperature and readily precipitated from the reaction mixture on cooling. Thus, the collection of the produced HATI of high purity can be accomplished by a simple operation without recrystallization. Advantageously, the by-products having an amide bond are not precipitated from such solvent(s).

The amount of the solvent(s) to be used is not less than about 0.025 liter, usually from about 0.025 to 2 liters (preferably from about 0.05 to 0.5 liter), per 1 mole (192 grams) of trimellitic acid anhydride. When the amount is smaller than about 0.025 liter, the precipitate of HATI is contaminated with unreacted starting materials, reaction intermediates and/or by-products. When the amount is larger than about 2 liters, HATI itself will be considerably kept in the liquid phase so as to lower the yield.

Characteristically, the reaction medium comprises water in addition to the said solvent(s). Such water may be present in the reaction system from the very beginning of the reaction. Alternatively, it may be originated from the water unavoidably by-produced in the course of the reaction. The presence of water in the reaction medium is effective in preventing the self-condensation of the starting materials as well as the esterification of the starting materials with the alcoholic hydroxyl groups which may exist in the solvent(s). Thus, the formation of by-products as impurities can be suppressed.

The amount of water to be present in the reaction medium is closely associated with the kinds of the solvent(s) as used. In case of the solvent(s) being of Group (A), the amount of water may be such as corresponds to the weight of the water to be by-produced in the reaction, and it is not necessarily required to incorporate water into the reaction system from the very beginning of the reaction. In case of the solvent(s) being of Group (B), it is usually necessary to incorporate water into the reaction system from the very beginning of the reaction. Thus, there is normally employed as the reaction medium a mixture of the solvent(s) and water having a water content of not less than about 5% by volume (at 25° C.), preferably about 5 to 99% by volume. Examples of preferred proportions of the solvent(s) and water are as follows:

| Reaction medium | Proportion (volume ratio at 25° C.) |
| --- | --- |
| Methanol : Water | 60:40–1:99 |
| Ethanol : Water | 60:40–1:99 |
| Ethylene glycol : Water | 90:10–1:99 |
| Ethylene glycol monomethyl ether : Water | 80:20–1:99 |
| Dioxane : Water | 90:10–1:99 |
| Acetone : Water | 50:50–1:99 |
| Dimethylformamide : Water | 50:50–1:99 |

For carrying out the reaction smoothly, there is usually employed a catalyst, of which examples are amines and their quaternary ammonium salts (e.g. triethylamine, N-dimethylbenzylamine, triethylenediamine, isoquinoline, N-methylmorpholine, pyridine, trimethylphenylammonium chloride). Among, them, pyridine is the most favorable.

The reaction temperature may be in the range of room temperature to 200° C. or higher, preferably in the range of about 70° to 280° C., especially of about 120° to 200° C. By conducting the reaction at a lower temperature, the yield is usually lower. In case of using a solvent having a low boiling point, the reaction may be carried out under an elevated pressure to keep a high reaction temperature or in the presence of the catalyst as stated above. The reaction time is usually from about 1 to several tens of hours.

By adopting the reaction conditions as stated above, the reaction proceeds through the stage where all of the starting materials, the reaction products including the intermediary compounds and the objective compound and the unfavorable by-products are perfectly dissolved in the reaction medium.

By cooling the reaction mixture, for instance, to room temperature or about 5° C., HATI is selectively precipitated as a solid. For facilitating the precipitation of HATI, the reaction medium may be partly eliminated by distillation during the reaction or after its completion. In this case, at least a part of the amount of water corresponding to that formed in the reaction system is required not to be eliminated but to remain in the reaction system. Preferably, the amount of water corresponding to that formed in the reaction system is made to remain so as to prevent formation of oligomers. In case of necessity, a large amount of water may be added to the hot or cooled reaction mixture after the reaction, or the reaction mixture may be poured into a large amount of water. The thus precipitated HATI is collected by filtration and dried well to remove the solvent and/or water completely. In case of using a solvent having a high boiling point, the collected precipitate of HATI may be washed with a mixture of methanol or ethanol and water (60:40–0:100, volume ratio at 25° C.) several times and then dried well to eliminate the solvent completely to obtain pure white crystals of HATI.

The thus prepared HATI has the following chemical structure:

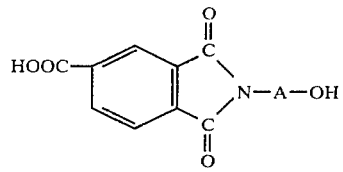

wherein A is an alkylene group (preferably not more than 5 carbon atoms). Identification of the reaction product may be effected by IR absorption spectrum, NMR spectrum and acid titration.

In case of HETI, for instance, the IR spectrum determined by the KBr method by the aid of an infrared spectrophotometer (Hitachi 285 type) shows the absorptions assignable to the hydroxyl group (3440 cm$^{-1}$ (O—H stretching vibration), 1010 cm$^{-1}$ and 1050 cm$^{-1}$ (C—O stretching vibration)), the absorptions assignable to the carboxyl group (3200 cm$^{-1}$–2500 cm$^{-1}$ (a series of characteristics O—H stretching vibration), 1695 cm$^{-1}$ (carboxylic C=O stretching vibration) and 1450 cm$^{-1}$(O—H in-plane deformation vibration)), the absorptions assignable to the imide ring (1772 cm$^1$ and 1730 cm$^{-1}$ (C=O stretching vibration), 730 cm$^1$) and other characteristic absorptions assignable to the benzene ring and methylene group. The absorptions attributed to a secondary amide group and an amine-carboxylate salt are not observed.

The NMR spectrum is determined at 70° C. in dimethyl-sulfoxide-d$_6$ as the solvent by the aid of Varian A-60. Only the absorptions characteristic to HETI are observed.

The acid titration is effected in a conventional manner by titrating a methanol solution of HETI with a methanol solution of potassium hydroxide in the presence of phenolphthalein as an indicator.

It is already known that the polycondensation of HATI can afford poly(alkylenetrimellitate imides) (hereinafter referred to as "PATI"). For instance, the polycondensation of HETI gives poly(ethylenetrimellitate imide) (hereinafter referred to as "PETI"). It is also known that fibers, woven cloths, unwoven cloths, knitted cloths, films, sheets and various molded products prepared from PATI show a high melting temperature and a high glass transition temperature and possess excellent mechanical properties (e.g. strength, modulus of elasticity) and a high chemical resistance. Thus, these materials are expected to be utilized as tire, cordes, insulating materials, magnetic tapes and the like.

On the other hand, the study on the relationship between the physical properties of PATI and the utilization of PATI has revealed that PATI should have preferably an intrinsic viscosity of at least 0.25 dl/g or more (preferably 0.35 dl/g or more) for production of fibers, an intrinsic viscosity of 0.3 dl/g or more (preferably 0.35 dl/g or more) for production of molded products and an intrinsic viscosity of 0.35 dl/g or more (preferably 0.4 dl/g or more) for production of films and sheets.

In conventional PETI (U.S. Pat. No. 3,060,191), a sufficiently high molecular weight for the said uses has never been obtained. Japanese Patent Publication (unexamined) No. 101491/1975 discloses a process for preparation of high molecular weight PETI. In this case, however, there is caused a problem of degradation (i.e. reduction of molecular weight) during the polymerization or during the molding.

As the result of the extensive study, there have now been completed the following methods:

(1) A method for preparation of PATI being hardly accompanied with degradation during melt polymerization, i.e. production of PATI having a high degree of polymerization by melt polymerization;

(2) A method for preparation of PATI being hardly accompanied with degradation during melt molding; and (3) A method for preparation of PATI showing an excellent color tone; i.e. PATI hardly accompanied with abnormal coloring.

The HATI prepared by the process of this invention is excellent in thermal stability and color tone and has high polymerization activity in comparison with HATI prepared by conventional processes, and it can be used advantageously as the starting monomer for production of PATI according to any of the above mentioned methods.

For polycondensation of HATI, there may be adopted any procedure conventionally employed for production of polyesters. Thus, the polycondensation can be carried out in the presence of a metal (e.g. titanium, antimony, germanium, bismuth, tin, lead) or its compound (e.g. alcoholates, oxides, carboxylates, hydrides, halides) as the catalyst at an elevated temperature under a reduced pressure while eliminating low molecular weight materials from the reaction system. The degree of polymerization may be elevated by effecting further polymerization in a solid phase. The use of HATI prepared by the process of the invention is particularly advantageous since it shows a higher polymerization activity compared with HATI prepared by any other process and affords PATI superior in color tone to that obtained from HATI prepared by any other process.

For obtaining PATI with a high degree of polymerization by melt polymerization, the selection of a suitable catalyst for polycondensation is important, and examples of a particularly preferred catalyst are a titanyl oxalate salt, a titanyl tartrate salt, etc. Examples of the salt of titanyl oxalate or titanyl tartrate are the ammonium salt and monovalent or divalent metal salts (e.g. calcium salt, strontium salt, barium salt, lead salt, zinc salt, sodium salt, potassium salt). Among them, potassium titanyl oxalate and potassium titanyl tartrate are particularly preferred. The amount of the catalyst to be used may be from about 0.001 to 0.5 mol % with respect to HATI. Prefeably, the catalyst is employed in an amount of about 0.05 mole % or less. The time for addition of the catalyst to the reaction system is not particularly limited. It may be added at the beginning of or during the polycondensation reaction. Two or more kinds of the catalysts may be used in combination. In case of necessity, a conventional catalyst for ester exchange or for polycondensation and a coloring-preventing agent (e.g. lead oxide, phosphorous acid) may be used together.

The said catalysts show a higher catalytic activity for polycondensation in comparison with other conventional catalysts. By the use of such catalyst, the following industrial advantages are brought about. Firstly, the producibility in the preparation of PATI can be increased. Secondly, since only a small amount of the catalyst is required for producing a unit amount (weight) of polymer at an industrially appropriate cycle time of polymerization, the content of ashes which may cause deficiency in insulation in case of using the produced polymer as films or sheets for insulation can be reduced in comparison with conventional polymers. Thirdly, potassium titanyl oxalate, ammonium titanium oxalate or potassium titanyl tartrate as the catalyst can be used only in a small amount, and besides, they exert in themselves a lesser poisonous activity against living bodies, compared with other conventional catalysts containing a heavy metal.

The HATI prepared by the process of the invention can afford PATI having a more excellent color tone than in case of using HATI obtained by conventional methods. By appropriate selection of the catalyst, the color tone of the produced PATI can be further improved. For this purpose, the use of bismuth trioxide, bismuth acetate or basic bismuth carbonate is particularly suitable. Although a catalyst exerting a high polymerization activity usually tends to color PATI, the said particular catalyst not only shows a high polymerization activity but also affords PATI having an excellent color tone. The amount of the catalyst to be used is usually from about 0.01 to 0.5 mole %, preferably from about 0.02 to 0.05 mole %, with respect to HATI. The time for addition of the catalyst is not particularly limited. It may be added at the beginning of or in the course of the polycondensation reaction. In case of necessity, a conventional catalyst for ester exchange or for polycondensation or a phosphorus compound may be incorporated into the reaction system. The PATI obtained by polycondensation of the HATI of the invention is excellent in thermal stability in addition to its good color tone.

For preventing the decrease of the molecular weight of PATI during melt molding, the reduction of the number of terminal carboxyl groups in PATI has a remarkable effect. In order to achieve such reduction, a carbonate compound, a carbodimide compound, an epoxy compound, an alcohol, a glycol or the like may be incorporated into PATI at the polycondensation or during molding. Incorporation of a compound having one or two alcoholic hydroxyl groups during the polycondensation is particularly preferred. The PATI obtained by incorporation of such compound has substantially the following structure:

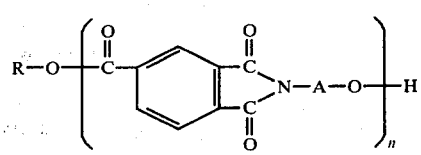

(I)

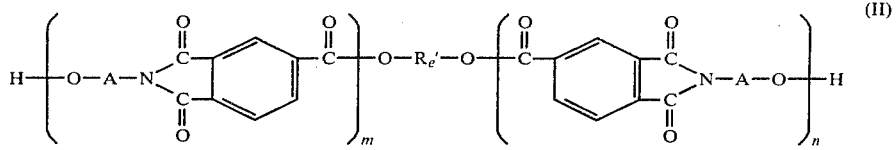

wherein R is an aliphatic or alicyclic alcohol residue having not more than 20 carbon atoms, $R_e'$ is a group of the formula:

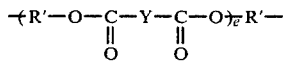

(e being zero or 1, Y is an aliphatic, alicylic, aromatic or heterocyclic dicarboxylic acid residue of 2 to 20 carbon atoms and R' is an alkylene glycol residue of 2 to 20 carbon atoms), m and n represent each a value at which the intrinsic viscosity of the polymer is not less than 0.25 dl/g, and A is as defined above.

Examples of the alcohol residue represented by R are residues of methyl alcohol, ethyl alcohol, n-butyl alcohol, n-hexyl alcohol, n-octyl alcohol, benzyl alcohol, ethylene glycol monomethyl ether, ethylene glycol monoethyl ether, ethylene glycol monobutyl ether, ethylene glycol monophenyl ether, etc. Examples of the dicarboxylic acid residue represented by Y are residue of phthalic acid, isophthalic acid, terephthalic acid, 2,6- or 2,7-naphthalene-dicarboxylic acid, biphenyldicarboxylic acid, sebacic acid, decanedicarboxylic acid, etc. Examples of the glycol residue represented by R' are residues of ethylene glycol, 1,4-butyleneglycol, neopentyl glycol, diethylene glycol, etc.

The amount of such a compound to be incorporated is usually about 10 mole % or less, preferably 5 mole % or less, (as OH) to HATI. When the amount is more than the said limit, the polymerization rate becomes small, and PATI with a high degree of polymerization is hardly obtainable. For attaining the purpose of the incorporation, 0.5 mole % or more of the compound is usually employed. By such procedure, PATI having a content of terminal carboxyl groups of not more than about 50 eq/$10^6$ g polymer can be readily prepared. Usually, the content of terminal carboxyl groups in the thus obtained PATI is in a range of 50 to 10 eq/$10^6$ g polymer.

The process for preparation of PATI according to the invention can be applied to the production of a copolymer modified with any other monomer(s) containing a group susceptible to polycondensation. Examples of such monomer are p-hydroxybenzoic acid, p-acetoxybenzoic acid, ε-caprolactone, ε-caprolactam, etc. It can be also applied to the case where a blocking agent for a terminal hydroxyl group such as a carboxylic acid or a chain-extending agent is employed.

The melt polycondensation may be carried out in an apparatus conventionally used for polycondensation of polyethylene terephthalate or a polymerization apparatus of bent extruder type suitable for production of a polymer of high melt viscosity. At the beginning of the polycondensation, it is desired to effect the reaction at a temperature in the range of from about 200° to 240° C. in the stream of an inert gas or under reduced pressure while distilling out water or the alcohol. It is then required to elevate gradually the temperature for the polymerization reaction with increase of the polycondensation degree of the polymer and to effect the polycondensation reaction finally at a temperature in the range of from about 270° C. to 330° C. under reduced pressure. When the polymerization temperature becomes higher than about 330° C., undesirable side reactions such as decomposition may be caused, which results in coloring of the polymer or decrease of the degree of polymerization.

In the melt polymerization, a polymer having an intrinsic viscosity of about 0.25 dl/g or more can be readily produced. In case of necessity, an intrinsic viscosity of 0.8 dl/g or more can be satisfactorily obtained. It is possible to suject the PATI (including oligomers) obtained by the melt polycondensation to further polymerization in a solid phase. In case of effecting such polymerization in a solid phase, the melt polymerization may be stopped in the state of an oligomer to initiate the subsequent polymerization in a solid phase. Prior to the polymerization in a solid phase, PATI is desired to be pulverized to a powder or pelletized and then to be treated with an organic solvent such as acetone or methanol at room temperature or under heating for crystallization. For preventing melt adhesion of the surfaces of pellets at the initial stage of the polymerization in the solid phase, it is desirable to give a large shearing force to the polymer at its isolation after the melt polymerization to obtain an oriented-crystallized PATI which is then subjected to the polymerization in a solid phase.

The polymerization in a solid phase may be carried out in an optional apparatus such as a conventional rotary type drying machine or a conventional fluidized bed type drying machine. In any case, it is necessary to prevent melt adhesion between particles of powder or pellets. For this purpose, the temperature for polymerization in a solid phase is preferably lowered. But, the polycondensation rate becomes small when the temperature is lowered. Therefore, it is preferred to initiate the reaction of polymerization in a solid phase at a temperature in the range of from about 150° to 170° C. and then to continue the reaction at a gradually elevated temperature, e.g. at about 170° to 190° C., at about 190° to 210° C., at about 210° to 240° C. and at about 240° to 270° C., until a resin having a desired intrinsic viscosity can be obtained. The temperature for melt adhesion is gradually raised with progress of crystallization of the resin and elevation of the temperature for softening. Therefore, the polymerization is preferably effected for a long time at the highest temperature permissible for preventing the melt adhesion so as to obtain a polymer with a high polymerization degree.

The PATI obtained by the process of the invention is utilizable as films, sheets, fibers, woven cloths, nonwoven fabrics, knitted products and other molded products, adhesives and paints in the fields where a thermal resistance or a mechanical strength or modulus of elasticity is required.

The PATI prepared according to the process of the invention may contain a crystal nucleus-forming agent, a filler, a pigment, glass fibers, carbon fibers, an antioxidant, a thermal stabilizer, a plasticizer, an ultraviolet ray-absorbing agent, a carboxyl group-blocking agent, a chain-extending agent and other additives and other resins (e.g. polyethylene terephthalate, polybutyleneterephthalate, nylon 6, nylon 66, polypropylene, fluorine resin, polysiloxane).

Practical and presently preferred embodiments of the invention are illustratively shown in the following Examples wherein % is by weight unless otherwise indicated. The determination of the physical properties shown in these Examples is effected by the following procedures:

(1) IR absorption spectrum:

The determination is carried out by the KBr tablet method using an infrared spectrophotometer (Hitachi 285 type manufactured by Hitachi, Ltd.).

(2) NMR spectrum:

The determination is carried out at 70° C. in a 15% dimethylsulfoxide-$d_6$ solution using an NMR spectrometer (Varian A-60 manufactured by Varian Assoc.).

(3) Nitrogen analysis:

An automatic determination apparatus for nitrogen (Callman 29 type) is used.

(4) Melting point of crystals:

The determination is carried out under a temperature elevating rate of 20° C./min by the use of a differential scanning calorimeter (manufactured by Perkin Elmer). The temperature affording a peak of thermal absorption is recorded. The amount of the specimen is 10 mg. The sensitivity is 8 mcal/sec.

(5) Intrinsic viscosity:

The determination is carried out at 30° C. in a solvent mixture of phenol-sym-tetrachloroethane (60:40 by weight) by the aid of an Ubbelohde's dilution viscometer.

(6) Color of polymer:

The resin is pulverized into a powder of 30 mesh or less and shaped into a tablet at room temperature under a pressure of 200 kg/cm$^2$ by the aid of a tablet-shaping machine, and the color tone of the obtained tablet is determined by the aid of a Hunter colorimeter (color-difference meter ND-101 D type manufactured by Nihon Denshoku K.K.). The results are shown by L valve (a larger value indicating a whiter tone), a value (a larger value in + indicating a more reddish tone) and b valve (a larger value in + indicating a more yellowish tone).

(7) Amount of terminal carboxyl groups in polymer:

The determination is effected according to the H. A. Pohl's method (Analytical Chemistry, 26, 1614 (1954)), but the polymer is dissolved by the following procedure: adding to the polymer (0.2 g) benzyl alcohol (5 ml) and heating at 215°±1° C. in an oil bath for 7 minutes under stirring. For washing, benzyl alcohol (5 ml) is added, and the mixture is heated at 215°±1° C. for 3 minutes. The results are indicated by [COOH] eq/10$^6$ g.

(8) Melt-liquidizing temperature of polymer:

The determination is carried out by the aid of a melting-boiling point-determining apparatus of FPI type (manufactured by Mettler) under a temperature-elevating velocity of 10° C./min. An ultramicro amount of specimen is observed by a microscope, and the temperature range from initiation of liquidization to its completion is recorded.

EXAMPLES 1 TO 11 AND REFERENCE EXAMPLES 1 TO 10

In a three-necked flask, trimellitic acid anhydride (96.06 g, 0.5 mole) is charged, and a solution of monoethanolamine (99.5%) (30.7 g, 0.5 mole) in a mixture of methanol and water (50:50 by volume) (100 ml) is added thereto. The mixture is stirred while raising gradually the temperature to obtain a uniform solution in about 1 hour. The temperature is further elevated to a reflux temperature (inner temperature, 83° C.). After 24 hours, heating is stopped, and the reaction is allowed to cool to 25° C. The precipitated white solid is collected by filtration, washed with a mixture of methanol and water (50:50 by volume) and dried at 90° C. under reduced pressure to obtain pure white crystals (80.5 g). Yield, 68.5%. Molecular weight (determined by acid titration), 239 (theoretical value, 235). Nitrogen content, 6.02±0.05% (theoretical value, 5.96%). This product is identified with HETI by the IR spectrum, the NMR spectrum and the nitrogen analysis.

In the same manner as above, the reaction is effected using different solvents under varied reaction conditions, and the results are shown in Table 1. In some of the Reference Examples, the produced water is eliminated without reflux. The mixing proportions on the solvent mixtures are all indicated as volume ratios at 25° C.

TABLE 1

| | Reaction condition | Yield (%) | Color tone | Amide linking*4 (1550 cm$^{-1}$) | Rate of esterification*1 (%) | Melting point (°C.) | Remarks |
|---|---|---|---|---|---|---|---|
| Example 1 | Methanol/water (50/50), 100 ml; reflux for 24 hours, allowed to cool for precipitation | 69 | Pure white | None | 0 | 207 | |
| Example 2 | Ethanol/water (50/50), 100 ml; reflux for 6 hours, allowed to cool for precipitation | 46 | Pure white | None | 0 | 208 | |
| Example 3 | Ethylene glycol, 250 ml; at 150° C. for 1.5 hours, cooled to 5° C. for precipitation, filtration at 25° C., washed with methanol/water (60/40) | 80 | Pure white | None | 0 | 210 | |
| Example 4 | Ethylene glycol/water (70/30), 365 ml; reflux for 4 hours, allowed to cool for precipitation, washed with methanol/water (50/50) | 66 | Pure white | None | 0 | 210 | |
| Example 5 | Benzyl alcohol, 250 ml; reflux for 1.2 hours, allowed to cool for precipitation, washed with methanol/water (50/50) | 82 | White | None | 0 | 207 | |
| Example 6 | Water, 75 ml; reflux for 6 hours, | 65 | Pure | None | 0 | 209 | |

TABLE 1-continued

| | Reaction condition | Yield (%) | Color tone | Amide linking*4 (1550 cm$^{-1}$) | Rate of esterification*1 (%) | Melting point (°C.) | Remarks |
|---|---|---|---|---|---|---|---|
| | allowed to cool for precipitation, washed with water | | white | | | | |
| Example 7 | Ethylene glycol/water (80/20), 300 ml; reflux for 5.8 hours, allowed to cool for precipitation, washed with methanol/water (50/50) | 67 | Pure white | None | 0 | 208 | |
| Example 8 | Acetone/water (50/50), 75 ml; reflux for 6 hours, allowed to cool for precipitation | 49 | Pure white | None | 0 | 209 | |
| Example 9 | Dioxane/water (50/50), 75 ml; reflux for 6 hours, allowed to cool for precipitation | 51 | Pure white | None | 0 | 208 | |
| Example 10 | Dimethylformamide/water (50/50), 75 ml; reflux for 6 hours, allowed to cool for precipitation | 68 | Pure white | None | 0 | 209 | |
| Example 11 | Dioxane, 75 ml; reflux for 6 hours, allowed to cool for precipitation | 80 | Light brown | None | 0 | 208 | |
| Reference Example 1 | Dimethylformamide, 250 ml; at 120° C. for 1.7 hours, elimination of solvent under reduced pressure at same temperature, recrystallized from dioxane (treated with active carbon) | 40 | Light brown | Observed before recrystallization | 0 | 194 (before recrystallization); 209 (after recrystallization) | Method of Japanese Pat. Pub. No. 21500/63 (Example M) |
| Reference Example 2 | Dimethylformamide, 500 ml; at 70° C. for 1 hour, elimination of solvent under reduced pressure at same temperature, further reaction under 4 mmHg at 70-150° C. for 40 minutes, at 150° C. for 45 minutes | — | Yellowish white | Observed (0.066) | 0 | 199 | Method of U.S. Pat. No. 3,060,191 UR value,*5 0.31 |
| Reference Example 3 | Dimethylformamide, 65 ml; at 150° C. for 55 minutes, elimination of solvent under reduced pressure at same temperature, further reaction under 20 mmHg at 150-200° C. for 30 minutes, at 200-270° C. for 45 minutes | — | Yellow | Observed (0.081) | 75 | No absorption | Method of Japanese Pat. Pub. (unexamined) No. 101491/75 (Example 1) |
| Reference Example 4 | Dimethylformamide, 100 ml; reflux for 2 hours, allowed to cool | — | — | — | — | — | Not precipitated by spontaneous cooling |
| Reference Example 5 | Acetone, 100 ml; reflux for 2 hours, allowed to cool | — | Pale yellow | — | — | — | Reaction product being precipitated before dissolution of TMA; isolation being impossible |
| Reference Example 6 | m-Cresol, 250 ml; at 190° C. for 5 hours (elimination of produced water), allowed to cool for precipitation, washed with acetone | —*2 | Gray | Observed (0.042, 3.6%) | 45 | 161, 185 | |
| Reference Example 7 | Tetralin, 250 ml; at 190° C. for 5 hours (elimination of produced water), allowed to cool for precipitation, washed with boiling acetone | —*2 | Gray | Observed (0.081) | 77 | 177 | |
| Reference Example 8 | Same as in Example 5 but produced water being continuously eliminated | 0*3 | — | Observed | *3 | — | |
| Reference Example 9 | Dissolution in methanol, 100 ml; elimination of methanol at 60° C. under reduced pressure, further reaction under 4 mmHg at 150° C. for 5 hours | —*2 | Pale yellow | Observed (0.082, 8.7%) | 22 | 194 | |
| Reference Example 10 | Water, 10 ml; bath temperature 100° C., for 6 hours, solidified during reaction, | 90 | White | Observed (0.032) | 0 | 204 | |

TABLE 1-continued

| Reaction condition | Yield (%) | Color tone | Amide linking*4 (1550 cm$^{-1}$) | Rate of esterification*1 (%) | Melting point (°C.) | Remarks |
|---|---|---|---|---|---|---|
| allowed to cool, washed with water | | | | | | |

Note:
*1 Molar ratio determined by NMR spectrum:

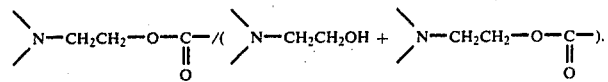

*2 Mixture with esterified product.
*3 Completely (100%) esterified (including benzyl alcohol ester).
*4 Determined by absorption at 1550 cm$^{-1}$ in IR spectrum. In the cases in which an absorption is observed at 1550 cm$^{-1}$, the numeral indicates the proportion of the absorbance at 1550 cm$^{-1}$ to the absorbance at 1772 cm$^{-1}$ (carbonyl in imide group). The parenthesized value (%) shows the proportion:

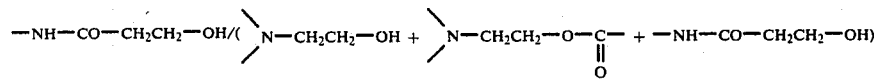

determined by NMR spectrum.
*5 Absorptions derived from reaction intermediates are observed at 6.8 τ- 7.4 τ in NMR spectrum. The proportion of (area in 6.8 τ-7.8 τ)/(area of methylene in

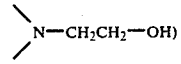

is indicated as the UR value.

EXAMPLE 12

In a 100 ml volume glass made reaction vessel equipped with a distillation apparatus and a stirring apparatus, HETI (23.52 g) obtained in Example 7 and potassium titanyl oxalate dihydrate (10.6 mg) are charged, and after the mixture is melted at 250° C. in a nitrogen stream, the reaction is carried out at the same temperature for 1 hour. The produced water is distilled out. Then, the pressure is gradually reduced to 3 mmHg, and the polycondensation reaction is continued at 250° C. for 30 minutes and then at 260° C. for 30 minutes. The temperature is elevated up to 290° C. in 15 minutes, and the polycondensation reaction is further continued at the same temperature for 30 minutes. Then, the reaction system is again placed in a nitrogen stream to effect sampling. The intrinsic viscosity of the produced polymer is 0.379 dl/g. After 5 minutes, the polycondensation reaction is again initiated and continued at 290° C. for 45 minutes under 3 mmHg. The thus produced polymer shows an intrinsic viscosity of 0.659 dl/g and a melt-liquidizing temperature of 259° to 265° C.

EXAMPLE 13

Using potassium titanyl oxalate dihydrate (5.3 mg) as the catalyst, the polycondensation reaction is carried out as in Example 12. The intrinsic viscosities after the reaction at 290° C. for 30 minutes and for 75 minutes are 0.380 dl/g and 0.616 dl/g, respectively.

EXAMPLE 14

Using ammonium titanium oxalate dihydrate (9.4 mg) as the catalyst, the polycondensation reaction is carried out as in Example 12. The intrinsic viscosities after the reaction at 290° C. for 30 minutes and for 75 minutes are 0.334 dl/g and 0.680 dl/g, respectively.

EXAMPLE 15

Using potassium titanyl tartrate (13.7 mg) as the catalyst, the polycondensation reaction is carried out as in Example 12. The intrinsic viscosity after the reaction at 290° C. for 90 minutes is 0.537 dl/g.

REFERENCE EXAMPLE 11

In the same manner as in Example 12, the polycondensation reaction is carried out using 0.03 mole % of antimony trioxide, germanium dioxide or lead monoxide in place of potassium titanyl oxalate dihydrate with respect to HETI. The intrinsic viscosities of the product 30 minutes and 75 minutes after the elevation of the reaction temperature to 290° are shown in Table 2.

TABLE 2

| Experiment | Catalyst | Intrinsic viscosity (dl/g) After 30 minutes | After 75 minutes |
|---|---|---|---|
| A | Potassium titanyl oxalate dihydrate ((Example 12) | 0.379 | 0.659 |
| B | Antimony trioxide | 0.375 | 0.512 |
| C | Lead monoxide | 0.216 | 0.304 |
| D | Germanium dioxide | 0.152 | 0.210 |
| E | None | 0.148 | 0.201 |

EXAMPLES 16 AND 17 AND REFERENCE EXAMPLES 12 TO 15

These Examples and the Reference Examples are presented for showing a higher polymerization activity of the monomer obtained in the invention in comparison with monomers obtained by other methods. Using different monomers and catalysts, the polymerization reaction is carried out under the same conditions as in Example 12. The results are shown in Table 3 wherein those in Example 13 are also given.

TABLE 3

| | Monomer used | Catalyst (mole %) | Intrinsic viscosity after reaction at 290° C. for 75 minutes |
|---|---|---|---|
| Example 13 | Obtained in Example 7 | Potassium titanyl oxalate dihydrate (0.015) | 0.616 |
| Reference | Obtained in Reference | Potassium titanyl oxalate dihydrate | 0.258 |

TABLE 3-continued

| | Monomer used | Catalyst (mole %) | Intrinsic viscosity after reaction at 290° C. for 75 minutes |
|---|---|---|---|
| Example 12 | Example 2 | (0.015) | |
| Reference Example 13 | Obtained in Reference Example 10 | Potassium titanyl oxalate dihydrate (0.015) | 0.328 |
| Example 16 | Obtained in Example 4 | Titanium tetrabutyrate (0.065) | 0.482 |
| Reference Example 14 | Obtained in Reference Example 3 | Titanium tetrabutyrate (0.065) | 0.367 |
| Example 17 | Obtained in Example 7 | Antimony trioxide (0.03) | 0.512 |
| Reference Example 15 | Obtained in Conventional Procedure* | Antimony trioxide (0.03) | 0.267 |

Note:
*Prepared by the procedure as described in Example 1 of Japanese Patent Publication (unexamined) No. 10149/1975. The reaction is effected by the following procedure: trimellitic acid anhydride (19.21 g) and antimony trioxide (8.7 mg) are dissolved in dimethylformamide (15 ml) at 150° C., and monoethanolamine (6.14 g) is added thereto. After the reaction is effected at 150° C. for 1 hour, dimethylformamide is distilled out under reduced pressure while elevating the temperature up to 250° C. in 30 minutes. Then, the reaction is continued under the same conditions as in Example 12.

EXAMPLE 18

This Example is presented for showing the superior color tone of the polymer prepared from the monomer of the invention in comparison with the color tone of the polymer prepared from the monomer obtained by a conventional method. The results are shown in Table 4.

TABLE 4

| | Color tone | | |
|---|---|---|---|
| Polymer used | L | a | b |
| Obtained in Example 17 | 57.9 | 8.4 | 20.6 |
| Obtained in Reference Example 15 | 33.8 | 5.2 | 11.2 |

EXAMPLE 19

This Example is presented for showing the superior color tone of the polymer obtained by the use of bismuth trioxide as the catalyst in comparsion with the color tones of the polymers obtained by the use of other catalysts. The monomer used is the one prepared in Example 7. The polymerization reaction is carried out under the same conditions as in Example 12. The results are shown in Table 5.

TABLE 5

| Experiment | Catalyst | Intrinsic viscosity after reaction at 290° C. for 75 minutes | Color tone | | |
|---|---|---|---|---|---|
| | | | L | a | b |
| A | Bismuth trioxide (0.03) | 0.501 | 69.3 | 1.2 | 16.0 |
| B | Potassium titanyl oxalate dihydrate (0.015) | 0.616 | 44.2 | 7.7 | 15.1 |
| C | Antimony trioxide (0.03) | 0.512 | 57.9 | 8.4 | 20.6 |
| D | Dibutyl tin dilaurate (0.03) | 0.453 | 63.5 | 8.3 | 19.9 |

EXAMPLE 20

This Example shows the production of PETI resin having a small content of terminal carboxyl groups.

Resin A

In a 100 ml volume glass made reaction vessel equipped with a distillation apparatus and a stirring apparatus, HETI (23.5 g) obtained in Example 4 and potassium titanyl oxalate dihydrate (3.54 mg) are charged, and the mixture is, after being melted at 250° C. in a nitrogen stream, stirred at the same temperature under 720 mmHg for 1 hour during which the produced water is eliminated. Then, the pressure is gradually reduced to 2 mmHg, and the polycondensation reaction is continued at 250° C. for 1 hour. The reaction system is again placed under a nitrogen stream, and after addition of bis-$\beta$-hydroxyethyl terephthalate (0.509 g), the reaction is further continued at the same temperature for 30 minutes under a reduced pressure of 720 mmHg. Then, the pressure is again reduced to 2 mmHg, and the polycondensation reaction is further continued at 260° C. for 1 hour, at 270° C. for 1 hour and then at 280° for 1 hour. The reaction mixture is rapidly cooled whereby a light orange polymer is obtained. After pulverization and drying (140° C., 1 mmHg, 5 hours), the product shows an intrinsic viscosity of 0.562 dl/g and a content of carboxyl group [COOH] of 49 eq/$10^6$ g.

Resin B

The reaction is effected in the same manner as mentioned above but changing the amount of bis-$\beta$-hydroxyethyl terephthalate to 1.017 g so as to obtain an intrinsic viscosity of 0.461 dl/g and a content of carboxyl group [COOH] of 40 eq/$10^6$ g.

Resin C

In a 100 ml volume glass made reaction vessel equipped with a distillation apparatus and a stirring apparatus, HETI (23.5 g) obtained in Example 4, potassium titanyl oxalate dihydrate (3.54 mg) and n-nonyl alcohol (1.443 g) are charged, and the mixture is, after being melted at 230° C. in a nitrogen stream, stirred at the same temperature for 1 hour in a nitrogen stream and then at 250° C. for 30 minutes. The produced water is distilled out. Then, the pressure is gradually reduced to 2 mmHg, and the polycondensation reaction is continued at 250° C. for 1 hour and 7 minutes, at 260° C. for 30 minutes, at 270° C. for 1 hour and 30 minutes, at 280° C. for 30 minutes and at 290° C. for 40 minutes. The reaction mixture is rapidly cooled whereby a light brown polymer is obtained. After pulverization and drying, the product shows an intrinsic viscosity of 0.419 dl/g and a content of carboxyl group [COOH] of 28 eq/$10^6$ g.

Resin D

In a 100 ml volume glass made reaction vessel equipped with a distillation apparatus and a stirring apparatus, HETI (23.5 g) obtained in Example 4, potassium titanyl oxalate dihydrate (3.54 mg) and neopentyl glycol (0.417 g) are charged, and the mixture is, after being melted at 230° C. in a nitrogen stream, stirred at the same temperature for 1 hour in a nitrogen stream and then at 250° C. for 30 minutes. The produced water is distilled out. Then, the pressure is gradually reduced to 2 mmHg, and the polycondensation reaction is continued at 250° for 30 minutes, at 260° for 1 hour, at 270° for 1 hour and 15 minutes, at 280° C. for 1 hour and 30 minutes and at 290° C. for 30 minutes. The reaction mixture is rapidly cooled whereby a light reddish orange polymer is obtained. After pulverization and drying, the product shows an intrinsic viscosity of 0.422 dl/g and a content of carboxyl group [COOH] of 20 eq/$10^6$ g.

Resin E (for reference)

In a 100 ml volume glass made reaction vessel equipped with a distillation apparatus and a stirring apparatus, HETI (23.5 g) obtained in Example 4 and potassium titanyl oxalate dihydrate (3.54 mg) are charged, and the mixture is, after being melted at 250° C. in a nitrogen stream, stirred at the same temperature for 1 hour. The produced water is distilled out. Then, the pressure is gradually reduced to 2 mmHg, and the polycondensation reaction is continued at 250° C. for 1 hour and 30 minutes, at 260° C. for 1 hour, at 270° C. for 1 hour and at 280° C. for 2 hours. The reaction mixture is rapidly cooled whereby a light brown polymer is obtained. After pulverization and drying, the product shows an intrinsic viscosity of 0.560 dl/g and a content of carboxyl group [COOH] of 79 eq/$10^6$ g.

Resin F (for reference)

In a 100 ml volume glass made reaction vessel equipped with a distillation apparatus and a stirring apparatus, HETI (23.52 g) obtained in Example 4 and intimony trioxide (8.8 mg) are charged, and the mixture is, after being melted at 250° C. in a nitrogen stream, stirred at the same temperature for 1 hour while eliminating the produced water. Then, the pressure is gradually reduced to 2 mmHg, and the polycondensation reaction is continued at 250° C. for 1 hour, at 260° C. for 1 hour, at 270° C. for 0.5 hour and at 280° C. for 1 hour, whereby a light orange polymer is obtained. Intrinsic viscosity, 0.440 dl/g. Content of carboxyl group [COOH], 122 eq/$10^6$ g.

EXAMPLE 21

This Example is presented for showing that the resin having a small content of terminal carboxyl groups is hardly degraded by heat.

Each of Resins A, D and E obtained in Example 20 is pulverized into a powder of 30 mesh or less and moistened at 20° C. under 65% RH to obtain a water content of 1.2 to 1.3%. The resin (1 g) is charged in a glass made ampoule, and after replacing the atmosphere by nitrogen, the ampoule is sealed by melting at room temperature under a nitrogen pressure of 700 mmHg (the capacity being about 15 ml). The ampoule is immersed into an oil bath kept at 288° ± 1° C. and allowed to stand still for 35 minutes. From the increase of the content of the terminal carboxyl groups, the breaking rate per 100 ester bonds in calculated. The results are shown in Table 6.

TABLE 6

| Resin | [COOH] (eg/$10^6$ g) | Breaking rate (%) |
|---|---|---|
| D | 20 | 1.1 |
| A | 49 | 1.4 |
| E | 79 | 1.7 |

EXAMPLE 22

In a 2 liter volume three-necked flask, trimellitic acid anhydride (384.2 g), isopropanolamine (150.2 g), ethylene glycol (300 ml) and water (300 ml) are charged, and the mixture is stirred for 8 hours under reflux and then allowed to cool overnight. Then, the precipitated solid is collected by filtration, washed with a mixture of methanol and water (50:50) (volume ratio at room temperature) and dried at 120° C. under reduced pressure whereby a pure white powder (323.6 g) is obtained. M.P. 213° C. Content of nitrogen, 5.40% (theoretical value of N-hydroxyisopropyltrimellitic acid imide being 5.62%).

The IR absorption spectrum of this powdery product shows the presence of hydroxyl group (3470 cm$^{-1}$, O—H stretching vibration; 1084 cm$^{-1}$, C—O stretching vibration), carboxyl group (3200 cm$^{-1}$ to 2500 cm$^{-1}$, a series of characteristic O—H stretching vibrations; 1700 cm$^{-1}$, carboxylic C=O stretching vibration and imide group (1772 cm$^{-1}$ and 1728 cm$^{-1}$, C=O stretching vibrations; 1402 cm$^{-1}$, imidic C—N stretching vibration; 735 cm$^{-1}$) as well as trisubstituted benzene nucleus, methyl group and methylene group. The absorption assignable to a secondary amide group or an amine-carboxylate salt is not observed.

In the NMR spectrum, the following absorptions are observed:

A: 1.63 τ, 1.76 τ, doublet (each split in 2 lines by the proton in carboxyl group);
B: 183 τ, singlet;
C: 2.06 τ, 2.19 τ, doublet;
D: 5.88 τ, 5.98 τ, 6.08 τ, 6.18 τ, quartet;
E: 6.45 τ, 6.56 τ, doublet (each split in 2 lines by the proton in hydroxyl group);
F: 8.86 τ, 8.95 τ, doublet.

These absorptions are respectively assigned to six kinds of hydrogen atoms in the following structural formula:

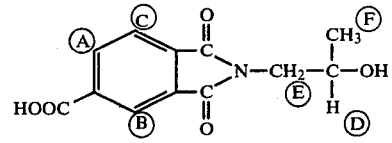

Thus, the product is identified with N-hydroxyisopropyltrimellitic acid imide according to the IR spectrum, the NMR spectrum and the nitrogen analysis.

What is claimed is:

1. A process for preparing a poly(alkylenetrimellitate imide) which comprises polycondensing an N-hydroxyalkyltrimellitic acid imide in the presence of at least one catalyst selected from the group consisting of a titanyl oxalate salt, a titanyl tartrate salt, bismuth trioxide, bismuth acetate and basic bismuth carbonate.

2. The process according to claim 1, wherein the catalyst is an ammonium, calcium, strontium, barium, lead, zinc, sodium or potassium salt of titanyl oxalate.

3. The process according to claim 1, wherein the catalyst is an ammonium, calcium, strontium, barium, lead, zinc, sodium or potassium salt of titanyl tartrate.

4. The process according to claim 1, wherein the catalyst is potassium titanyl oxalate.

5. The process according to claim 1, wherein the catalyst is potassium titanyl tartrate.

6. The process according to claim 2, wherein the amount of catalyst is about 0.001 to 0.5 mole % with respect to the amount of the N-hydroxyalkyltrimellitic acid imide.

7. The process according to claim 1, wherein the catalyst is bismuth trioxide, bismuth acetate or basic bismuth carbonate.

8. The process according to claim 7, wherein the amount of catalyst is about 0.01 to 0.5 mole % with respect to the amount of the N-hydroxyalkyltrimellitic acid imide.

9. The process according to claim 7, wherein the amount of the catalyst is about 0.02 to 0.05 mole % with respect to the amount of the N-hydroxyalkyltrimellitic acid imide.

* * * * *